US00PP25698P3

(12) United States Plant Patent
Ferguson et al.

(10) Patent No.: US PP25,698 P3
(45) Date of Patent: Jul. 14, 2015

(54) STRAWBERRY PLANT NAMED 'DRISSTRAWTHIRTYSIX'

(50) Latin Name: *Fragaria×ananassa*
Varietal Denomination: DrisStrawThirtySix

(71) Applicant: DRISCOLL STRAWBERRY ASSOCIATES, INC., Watsonville, CA (US)

(72) Inventors: Michael D. Ferguson, Moorpark, CA (US); Terrance C. Moran, Naples, FL (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 133 days.

(21) Appl. No.: 13/998,113

(22) Filed: Oct. 2, 2013

(65) Prior Publication Data

US 2015/0096086 P1 Apr. 2, 2015

(51) Int. Cl.
*A01H 5/08* (2006.01)

(52) U.S. Cl.
USPC ..... Plt./208

(58) Field of Classification Search
USPC ..... Plt./208
See application file for complete search history.

*Primary Examiner* — Susan McCormick Ewoldt
(74) *Attorney, Agent, or Firm* — Jondle & Associates, P.C.

(57) ABSTRACT

A new and distinct variety of strawberry plant named 'DrisStrawThirtySix' particularly characterized by a very vigorous plant bearing large, conic shaped fruit having an early harvest maturity is disclosed.

3 Drawing Sheets

Genus and species: *Fragaria×ananassa.*
Variety denomination: 'DrisStrawThirtySix'.

BACKGROUND OF THE NEW PLANT

The present invention relates to a new and distinct strawberry variety designated 'DrisStrawThirtySix' and botanically known as *Fragaria×ananassa.* This new strawberry variety was discovered in Ventura County, Calif. in January 2009 and originated from a cross between the proprietary female parent '101P292' (unpatented) and the proprietary male parent '73P176' (unpatented). A single plant was selected for asexual propagation via tissue culture and vegetative cuttings in Shasta County, Calif. in 2009.

'DrisStrawThirtySix' underwent further testing in Ventura County, Calif. for three years (2010-2012). The present invention has been found to retain its distinctive characteristics through successive asexual propagations via stolons and tissue culture.

Plant Breeder's Rights for this variety have not been applied for. 'DrisStrawThirtySix' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Ventura County, Calif.

1. Very vigorous plant;
2. Large, conic shaped fruit; and
3. Early harvest maturity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from seven-month-old plants.

DESCRIPTION OF THE NEW VARIETY

Figure 1:
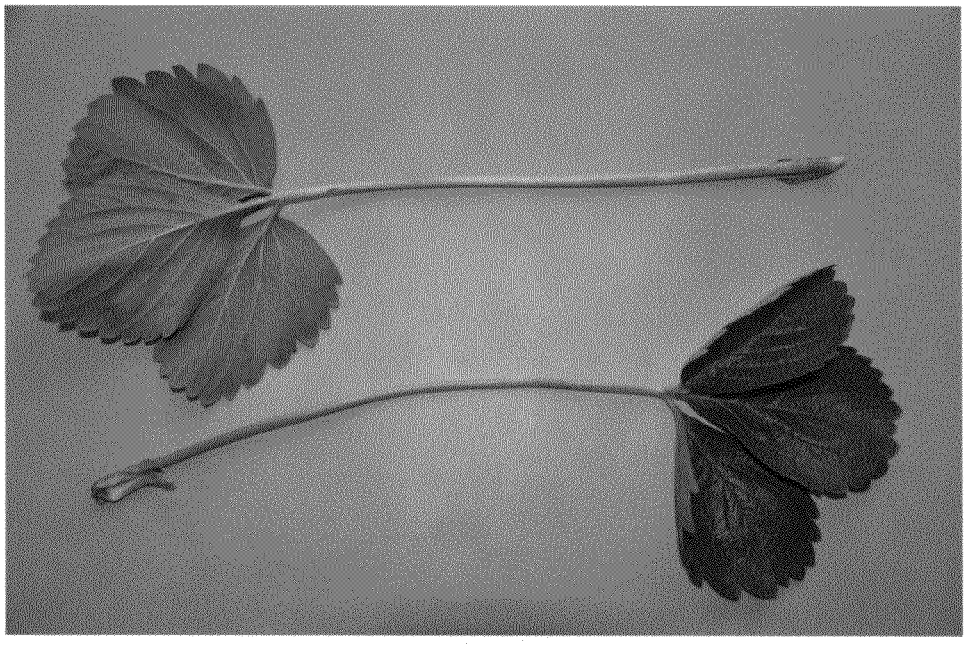
FIG. 1 shows upper and lower surfaces of the leaves of the plant with three leaflets.
Figure 2:
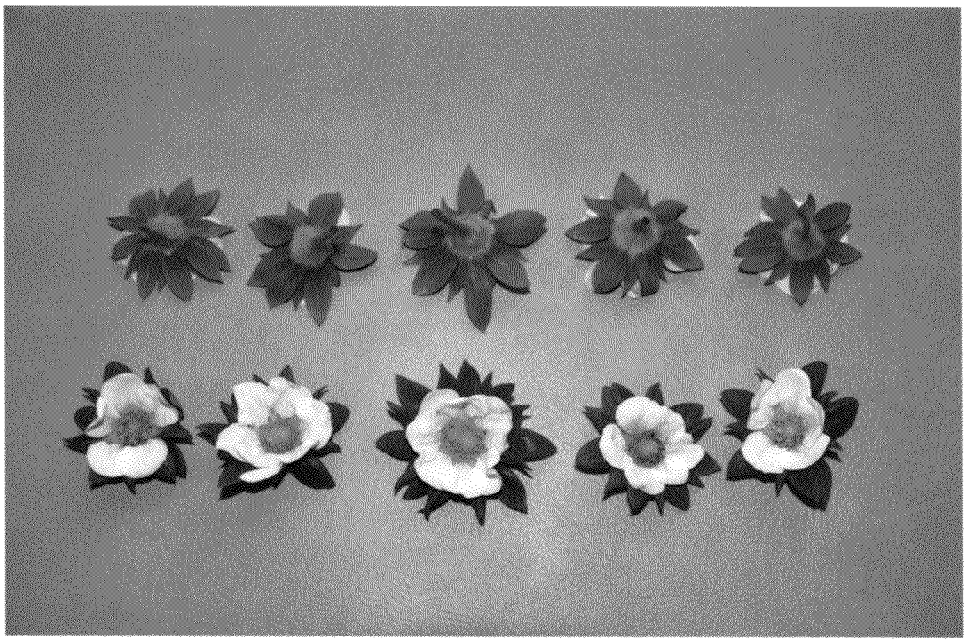
FIG. 2 shows both upper and lower surfaces of the flowers.
Figure 3:
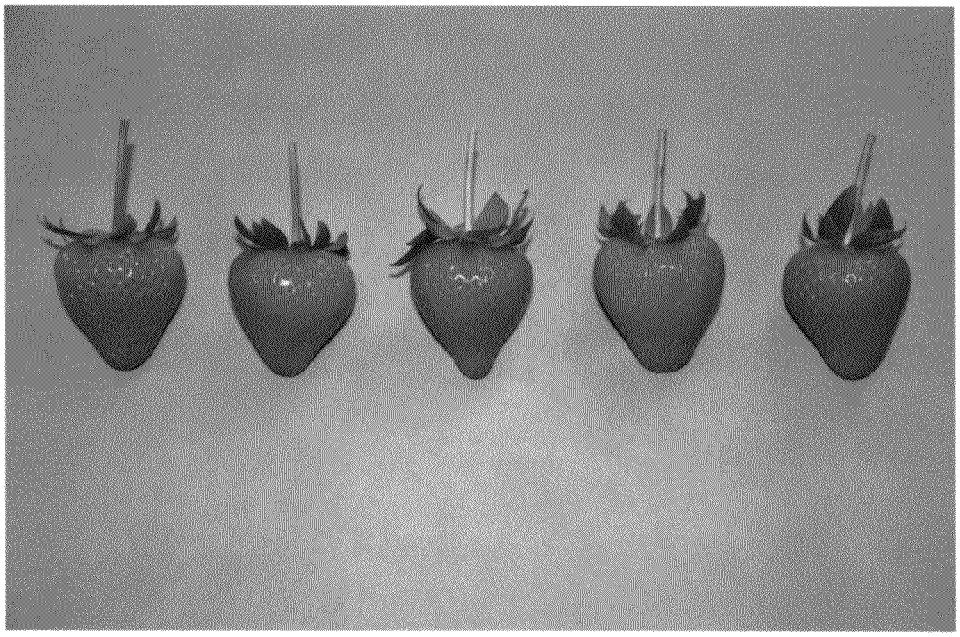
FIG. 3 shows the whole fruit.
Figure 4:
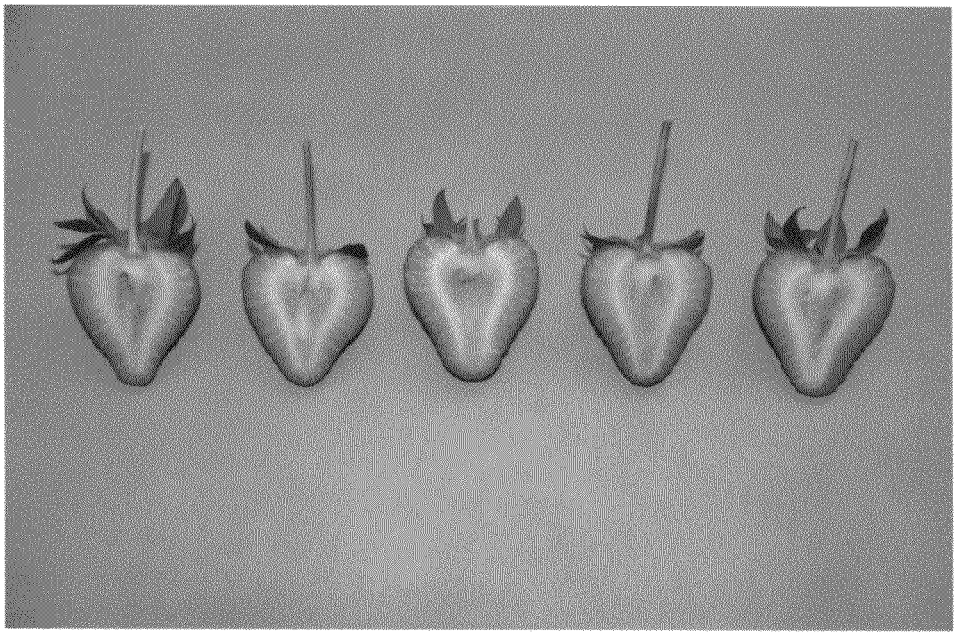
FIG. 4 shows the fruit in longitudinal cross-section.
Figure 5:
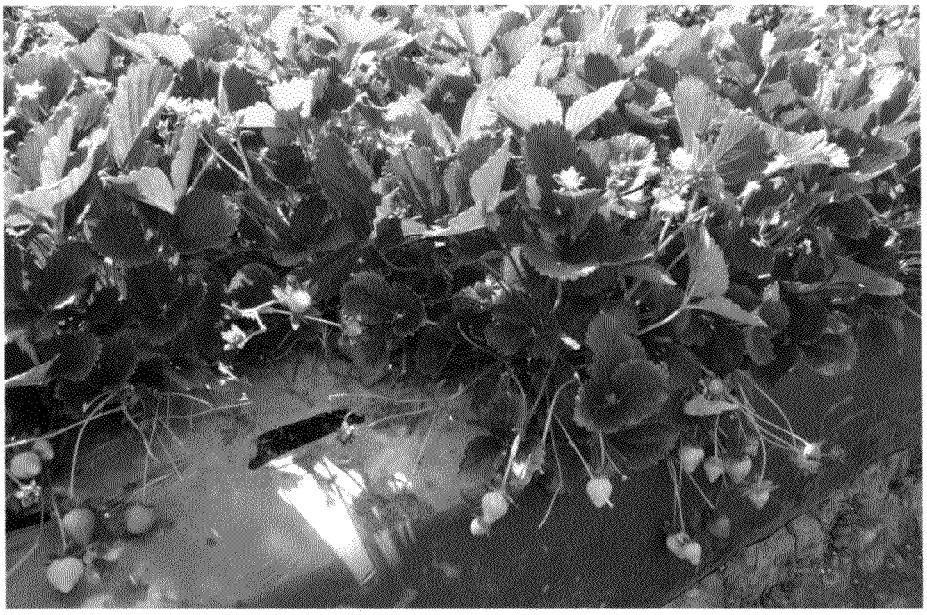
FIG. 5 shows the whole plant.

The following detailed descriptions set forth the distinctive characteristics of 'DrisStrawThirtySix'. The data which define these characteristics is based on observations taken in Ventura County, Calif. from 2010 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirtySix' has not been observed under all possible environmental conditions. The botanical description of 'DrisStrawThirtySix' was taken from seven-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawThirtySix'.

Parentage:
*Female parent.*—The proprietary variety '101P292' (unpatented).
*Male parent.*—The proprietary variety '73P176' (unpatented).
Plant:
*Height.*—35.4 cm.
*Diameter.*—60.1 cm.
*Number of crowns/plant.*—4.
*Habit.*—Globose — semi-upright.
*Density of individual plant.*—Dense.
*Vigor* (*health and hardiness of plant*).—Very strong.
Terminal leaflets:
*Size.*—Medium. Length: 10.0 cm. Width: 8.2 cm. Length/width ratio: 1.2 (Longer than broad).
*Number of teeth/terminal leaflet.*—16.
*Shape of teeth.*—Rounded to crenate.
*Color.*—Upper surface: RHS 147A (Dark yellow-green). Lower surface: RHS 148B (Medium yellow-green).
*Shape in cross section.*—Slightly concave.
*Blistering.*—Weak.
*Glossiness.*—Medium.
*Number of leaflets.*—Three only.
*Shape.*—Oval.
*Base shape.*—Acute.
*Apex descriptor.*—Rounded.
*Variegation.*—Absent.
*Margin.*—Crenate.
*Margin profile.*—Revolute and flat.
Petiole:
*Length.*—Long; 22.0 cm.
*Diameter.*—3.36 mm.
*Pubescence.*—Absent or very sparse.
*Pose of hairs.*—Slightly upwards.
*Color.*—RHS 144C (Medium yellow-green).
*Bract frequency.*—0.
Petiolule:
*Length.*—10.34 mm.
*Diameter.*—1.99 mm.
*Color.*—RHS 144D (Light yellow-green).
Stipule:
*Length.*—3.1 cm.
*Width.*—7.54 mm.
*Pubescence.*—Absent or very sparse.
*Stipule anthocyanin coloration.*—Absent or very weak; RHS 185B (Medium greyed-purple).
Stolon:
*Number.*—Medium.
*Average number of daughter plants.*—32.
*Stolon anthocyanin.*—Medium; RHS 170A (Medium greyed-orange).
*Diameter at bract.*—2.96 mm.
*Thickness.*—Thick.
*Pubescence.*—Sparse.
Inflorescence:
*Position relative to foliage.*—Above.
*Number of flowers.*—Many.
*Time of flowering* (*50% of plants at first flower*).—Medium.
*Flower size.*—Large.
*Diameter.*—29.63 mm.
*Petals.*—Shape: Orbicular. Apex: Rounded. Base: Concavo-convex. Margin: Entire. Spacing: Overlapping. Length: 14.80 mm. Width: 14.10 mm. Length/width ratio: 1.0 (As long as broad). Petal number per flower: 6. Color (upper surface): RHS NN155D (White).
*Calyx.*—Diameter: 38.15 mm. Diameter relative to corolla: Larger. Inner calyx diameter relative to outer: Smaller. Insertion of calyx: Level. Pose of calyx segments: Spreading to outwards and reflexed to upwards. Size of calyx in relation to fruit: Slightly larger. Adherence of calyx: Very strong.
*Sepal.*—Shape: Oval (outer) and elliptical (inner). Apex: Convex. Margin: Entire. Length: 14.91 mm. Width: 8.01 mm. Sepal number: 12.
*Receptacle color.*—RHS 1B (Medium yellow-green).
*Stamen.*—Present. Anther color: RHS 13A (Medium yellow).
*Pedicel.*—Attitude of hairs: Upwards to slightly upwards.
Fruiting truss:
*Length.*—Long; 30.9 cm.
*Diameter at base of truss.*—3.72 mm.
*Number of berries per fruiting truss.*—4.
*Attitude at first picking.*—Prostrate.
*Color at base of truss.*—RHS 144C (Medium yellow-green).
Fruit:
*Relative fruit size.*—Large.
*Length.*—45.55 mm.
*Width.*—40.48 mm.
*Length/width ratio.*—1.1 (Longer than broad).
*Fruit hollow length.*—21.46 mm.
*Fruit hollow width.*—10.19 mm.
*Fruit hollow length/width ratio.*—2.1 (Much longer than broad).
*Fruit hollow center* (*cavity*).—Medium.
*Weight* (*per individual berry*).—28.3 g.
*Predominant fruit shape.*—Conical.
*Difference in shape between primary and secondary fruits.*—Moderate.
*Evenness of fruit surface.*—Even or very slightly uneven.
*Fruit skin color.*—RHS 45A (Medium red).
*Evenness of fruit color.*—Even or very slightly uneven.
*Fruit glossiness.*—Strong.
*Achenes.*—Insertion of achenes: Below surface. Coloration (sunward side of berry): RHS 143C (Medium green). Coloration (shaded side of berry): RHS N144B (Medium yellow-green). Number per berry: 189. Weight (weight of achenes divided by total # seed): 0.00043978 g. Width of band without achenes: Medium.
*Firmness of flesh* (*when fully ripe*).—Firm.
*Color of flesh* (*excluding core*).—RHS 42A (Dark red).
*Color of core.*—RHS 48B (Medium red) and RHS NN155C (White).
*Evenness of flesh color.*—Even.
*Distribution of flesh color.*—Marginal and central.
*Sweetness.*—Medium.
*Acidity.*—Medium.
*Texture when tasted.*—Fine.
*Type of bearing.*—Not everbearing — not remontant.
*Grams of fruit/plant.*—1026.0 g.
*Harvest interval.*—Mid-December to June.
*Harvest maturity.*—Early.

Disease and pest resistance:

*Tetranychus urticae.*—Moderately susceptible.

*Tarsonemus pallidus.*—Moderately susceptible.

*Aphelencoides fragariae.*—Moderately susceptible.

*Pratylenchus penetrans.*—Moderately susceptible.

*Ditylenchus dipsac.*—Moderately susceptible.

*Anthonomus rubi.*—Moderately susceptible.

*Aphis spp.* (*Aphids*).—Moderately susceptible.

*Lygus hesperus* (*Lygus bug*).—Moderately susceptible.

*Botrytis fruit rot.*—Moderately susceptible.

*Powdery mildew.*—Moderately susceptible.

*Verticillium wilt.*—Moderately susceptible.

*Leather rot.*—Moderately susceptible.

*Leaf spots* (*Ramularia tulasnei*).—Moderately susceptible.

*Xanthomonas fragariae.*—Moderately susceptible.

Reaction to stress:

*High pH.*—Moderately resistant.

*High soil salt levels.*—Moderately resistant.

COMPARISON WITH PARENTAL AND COMMERCIAL VARIETIES

When 'DrisStrawThirtySix' is compared to the female parent '101P292' (unpatented), 'DrisStrawThirtySix' has higher yields and better fruit appearance than '101P292'.

When 'DrisStrawThirtySix' is compared to the male parent '73P176' (unpatented), 'DrisStrawThirtySix' has better flavor, firmer fruit and a more conic shape the '73P176'.

When 'DrisStrawThirtySix' is compared to the commercial variety 'Driscoll El Dorado' (U.S. Plant Pat. No. 16,238), 'DrisStrawThirtySix' has an acute terminal leaflet base, a moderate difference in shapes between primary and secondary fruits, and fruit that has a fine texture when tasted, whereas 'Driscoll El Dorado' has a rounded terminal leaflet base, a slight difference in shapes between primary and secondary fruits, and fruit that has a medium texture when tasted. Additionally, 'DrisStrawThirtySix' is moderately susceptible to *Tetranychus urticae*, whereas 'Driscoll El Dorado' is susceptible to *Tetranychus urticae.*

When 'DrisStrawThirtySix' is compared to the commercial variety 'DrisStrawTwentySeven' (U.S. Plant Pat. No. 23,400), 'DrisStrawThirtySix' has a globose to semi-upright habit on a dense plant with very strong vigor, whereas 'DrisStrawTwentySeven' has a flat globose habit on a medium dense plant with medium vigor. Additionally, 'DrisStrawThirtySix' has large fruit with a medium hollow center, whereas 'DrisStrawTwentySeven' has very large fruit with a large hollow center.

We claim:

1. A new and distinct variety of strawberry plant named 'DrisStrawThirtySix' as described and shown herein.

* * * * *